United States Patent
Jones et al.

(10) Patent No.: US 6,792,795 B2
(45) Date of Patent: Sep. 21, 2004

(54) SYSTEM AND METHOD FOR DETECTING HAZARDOUS MATERIALS USING AGITATION

(75) Inventors: Allen M. Jones, Kensington, MD (US); Clifford A. Megerle, Thousand Oaks, CA (US); John T. Swider, Port Crane, NY (US); Barry Wake, Remington, VA (US)

(73) Assignee: Lockheed Martin Corporation, Bethesda, MD (US)

(*) Notice: Subject to any disclaimer, the term of this patent is extended or adjusted under 35 U.S.C. 154(b) by 0 days.

(21) Appl. No.: 10/649,533

(22) Filed: Aug. 27, 2003

(65) Prior Publication Data

US 2004/0045342 A1 Mar. 11, 2004

Related U.S. Application Data

(63) Continuation-in-part of application No. 10/277,069, filed on Oct. 21, 2002, said application No. 10/649,533, is a continuation-in-part of application No. 10/201,169, filed on Jul. 22, 2002.
(60) Provisional application No. 60/344,848, filed on Dec. 31, 2001, and provisional application No. 60/330,673, filed on Oct. 26, 2001.

(51) Int. Cl.$^7$ ............................................. G01N 33/00
(52) U.S. Cl. .................... 73/37; 73/864.33; 73/23.2; 422/123
(58) Field of Search .................... 73/37, 864.33, 73/23.2; 422/123

(56) References Cited

U.S. PATENT DOCUMENTS

| | | | |
|---|---|---|---|
| 3,915,339 A | | 10/1975 | Matson |
| 3,942,357 A | * | 3/1976 | Jenkins ........................ 73/31.07 |
| 3,998,101 A | * | 12/1976 | Bradshaw et al. ............ 73/864 |
| 4,111,049 A | * | 9/1978 | Lerner et al. ................ 73/864.73 |

(List continued on next page.)

FOREIGN PATENT DOCUMENTS

| | | |
|---|---|---|
| JP | 02159554 | 12/1988 |
| WO | WO 91/09307 | 6/1991 |

OTHER PUBLICATIONS

Copending application Ser. No. 10/277,069 filed Oct. 21, 2002.

(List continued on next page.)

*Primary Examiner*—Hezron Williams
*Assistant Examiner*—Rodney T Frank
(74) *Attorney, Agent, or Firm*—Perkins Smith & Cohen LLP; Harvey Kaye; Jacob N. Erlich

(57) ABSTRACT

A system and method for detecting contaminants in or on objects, having a movably mounted container for holding objects and having a plurality of perforations and an entrance opening through which objects may be placed into the container. A housing encloses the container and forms a barrier to ambient air. There is a sealable opening for inserting and removing objects from the container. A drive assembly moves the container within the housing to move objects therein for emitting particles which are in or on such object. There is an air stream for moving air through the housing and container to entrain any emitted particles into the air stream and a sensor for sensing contaminants in the air stream and providing a signal when a contaminant is sensed. The container can be a rotatable cage or a vibrating box. In the method, there is a chamber provided which may be sealed with respect to ambient air to create an enclosed atmosphere. A plurality of objects are loaded into or onto a perforated container disposed within the enclosed atmosphere and an air stream is created within the enclosed atmosphere. The objects are agitated to cause them to emit particles therefrom into the air stream is tested to determine whether it contains any contaminants. If so, a signal is provided.

20 Claims, 17 Drawing Sheets

U.S. PATENT DOCUMENTS

| | | |
|---|---|---|
| 4,580,440 A | 4/1986 | Reid et al. |
| 4,718,268 A | 1/1988 | Reid et al. |
| 4,764,351 A | 8/1988 | Hennebet et al. |
| 4,987,767 A | 1/1991 | Corrigan et al. |
| 5,109,691 A | 5/1992 | Corrigan et al. |
| 5,322,603 A | 6/1994 | Kameda et al. |
| 5,345,809 A | 9/1994 | Corrigan et al. |
| 5,465,607 A | 11/1995 | Corrigan et al. |
| 5,470,546 A | 11/1995 | Hall |
| 5,585,575 A | 12/1996 | Corrigan et al. |
| 5,591,117 A | 1/1997 | Zelno |
| 5,700,426 A | 12/1997 | Schmitthaeusler et al. |
| 5,841,038 A | 11/1998 | Volz |
| 5,859,362 A | 1/1999 | Neudorfl et al. |
| 5,942,699 A | 8/1999 | Ornath et al. |
| 6,159,422 A | 12/2000 | Graves et al. |
| 6,183,950 B1 | 2/2001 | Madonna et al. |
| 6,295,860 B1 | 10/2001 | Sakairi et al. |
| 6,324,927 B1 | 12/2001 | Ornath et al. |
| 2002/0124664 A1 | 9/2002 | Call et al. |
| 2002/0126008 A1 | 9/2002 | Lopez et al. |
| 2003/0086821 A1 | 5/2003 | Matthews |

OTHER PUBLICATIONS

Copending application Ser. No. 10/201,169 filed Jul. 22, 2002.

Copending application, Ser. No. 10/282,977 filed Oct. 29, 2002.

Copending application, Ser. No. 10/314,631 filed Dec. 9, 2002.

Copending application, Ser. No. 10/341,033, filed Jan. 23, 2002.

Copending application, Ser. No. 10/328,230 filed Dec. 23, 2002.

Copending application, Ser. No. 10/328,264 filed Dec. 23, 2002.

Copending application, Ser. No. 10/289,810 filed Nov. 7, 2002.

Provisional application Ser. No. 60/330,673 filed Oct. 26, 2001.

Provisional application Ser. No. 60/344,848 filed Dec. 31, 2001.

* cited by examiner

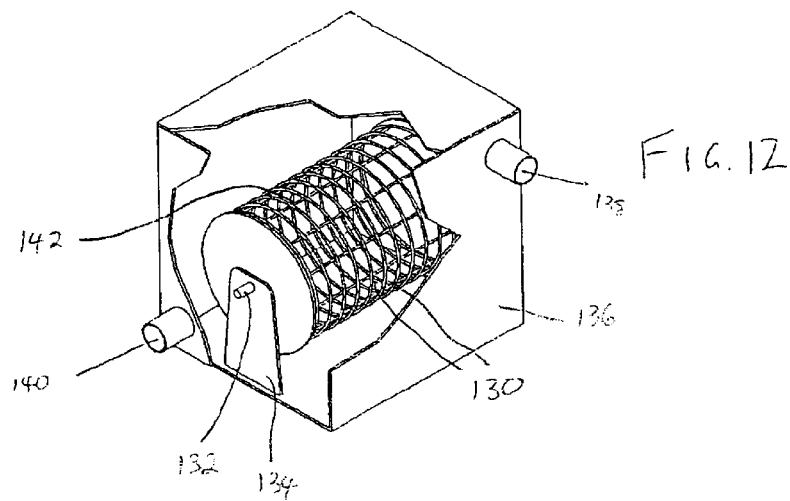
FIG. 12
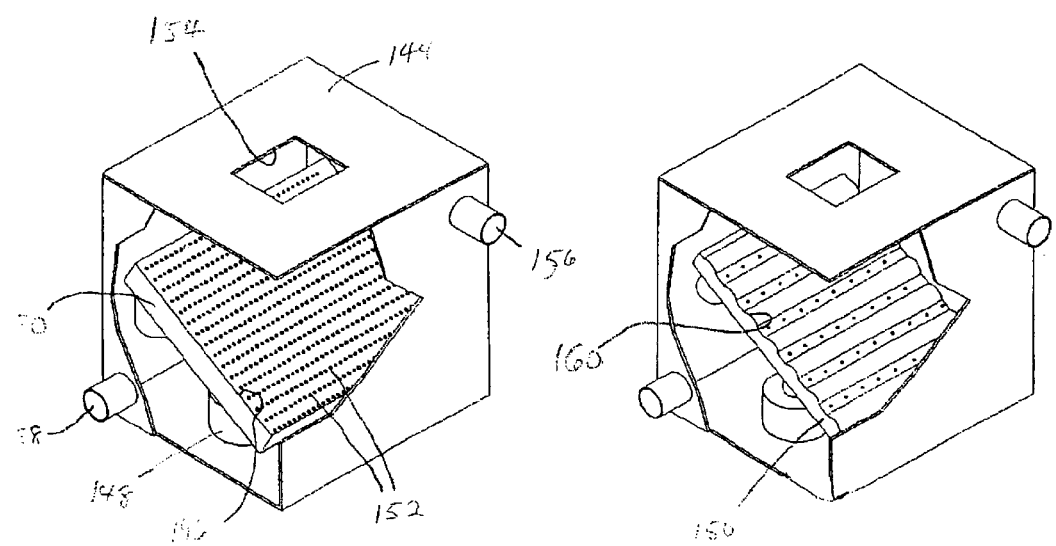
FIG. 13
FIG. 14

SYSTEM AND METHOD FOR DETECTING HAZARDOUS MATERIALS USING AGITATION

CROSS-REFERENCE TO RELATED APPLICATIONS

The present application is a continuation-in-part of application Ser. No. 10/277,069 filed Oct. 21, 2002 for System and Method For Detecting Hazardous Materials Inside Containers, which claims the benefit of provisional application Serial No. 60/330,673 filed Oct. 26, 2001 and a continuation-in-part of application Ser. No. 10/201,169 filed Jul. 22, 2002 for Closed Loop System For Air Sampling Of Contained Mail Products, which claims the benefit of provisional application Serial No. 60/344,848 filed Dec. 31, 2001, and the entire contents of all such applications are incorporated herein by reference.

BACKGROUND OF THE INVENTION

The present invention relates to a system and method for detecting hazardous materials inside articles and, more particularly, to a system and method for detecting hazardous materials inside mail.

All economies depend upon the physical shipment of materials for their functioning including the shipment of mail, merchandise, raw materials, and other goods.

In some circumstances, it is desirable to subject the goods to some type of inspection to determine the presence of hazardous or impermissible materials, including biological and chemical materials. In general, sophisticated sensing systems are known for the detection of hazardous biological and chemical materials. For example, such systems can include conventional laboratory facilities as well as mobile or semi-mobile units that can automatically or semi-automatically detect the presence of the undesired substance or substances. One such vehicle-mobile system is the Joint Biological Point Detection System (JBPDS) developed for the United States military and designed to detect the presence of a number of biological pathogens. Others include sensor or detectors for hazardous chemicals, explosives, illicit drugs, radioactive particles, and other hazardous materials. These sensors can be used single, or in combinations, to detect as many types of hazardous particles or vapors as required.

Currently when there is suspicious mail, it is all bulk irradiated, as was done during the recent anthrax problem in the U.S., thereby delaying some mail for months and damaging or destroying some of the mail due to problems caused by the irradiation. For example, some of this irradiated mail becomes brittle and pieces break off.

U.S. Published Application No. US 2002/0126008 published Sep. 12, 2002 and filed Oct. 31, 2001 discloses use of sensors at various locations within a typical mail processing system to sense the presence of a harmful agent. This system is completely open to the ambient atmosphere. (The present application is based upon a provisional patent application filed Oct. 26, 2001.)

U.S. Published Application No. US 2002/0124664 published Sep. 12, 2002 and filed Feb. 1, 2002 discloses use of a mail sampling system used in a room separate from the remainder of a post office facility and in which there is an air intake fan and all outgoing air is filtered before release. Most often openings are formed in the parcels and mail for the sampling. The sampling system is said to determine whether mail is contaminated with a chemical or biological agent. (The present application is based upon a provisional patent application filed Oct. 26, 2001.)

U.S. Pat. Nos. 5,942,699 and 6,324,927 disclose a manner of collective sampling of cargo items for contaminants such as chemical residues. The cargo items are placed into a special airtight chamber and physically agitated, such as by vibration, to release particulates and vapors from the items, and bursts of high pressure air is sent into the chamber. Heated air may also be used.

U.S. Pat. No. 3,915,339 discloses use of pressurized air into a container to loosen and cause free flow of material therein move.

U.S. Pat. No. 3,998,101 discloses a method and apparatus for sampling the atmosphere in non-hermetically-sealed containers by enclosing baggage in a chamber and varying the air pressure cyclically to mix a portion of the air in the baggage with the air in the chamber and a vapor detector is used to detect the presence of explosives or drugs in the baggage.

U.S. Pat. No. 4,580,440 discloses a method of detecting a contraband substance in freight cargo in which the container is agitated to disturb particulates therein and samples are taken of the air containing such particulates. The collected particulates are heated to drive off vapors indicative of the contraband substance and the vapors are analyzed in a mass analyzer.

U.S. Pat. No. 4,718,268 discloses a method and apparatus for detecting a contraband substance in freight cargo similar to that of U.S. Pat. No. 4,580,440 mentioned above.

U.S. Pat. No. 5,841,038 discloses a remote sampling device for possibly hazardous content of a container. A hollow needle punctures the container and is used to withdraw the contents or to introduce another substance. An inert gas can be introduced into the area where the needle punctures the container.

U.S. Pat. No. 5,859,362 discloses a trace vapor detection method and device of sampling a volume of air suspected of containing drug vapors, removing particulate matter and binding vapors of the drug for further analysis. The device has sampling, filtration and vacuum port components.

U.S. Pat. No. 6,295,860 for explosive detection system and sample collecting device in which luggage enters the device and leaves the device after inspection in which a vapor leaking from the luggage is sampled by a sampling probe, negative corona discharge is used to ionize the vapor, and a mass spectrometer is used to detect the ionized vapor to determine whether or not an explosive is present.

Patent Abstracts of Japan Pub. No. 02159554 A published Dec. 12, 1988, Application No. 63313358 discloses a monitoring method of a pathogen or allergen in which a biosensor is provided near a suction port for air conditioning provided for each room of wall surface which tends to gather mold.

WO 91/09307 published Jun. 27, 1991, for Explosive Detection Screening System detects vapor or particulate emissions from explosives and other controlled substances and reports their presence and may also report the concentration. There is a sampling chamber for collection of vapors or other controlled substances and a concentration and analyzing system, and a control and data processing system for the control of the overall system. There are a number of U.S. patents in this series, including the following: U.S. Pat. Nos. 4,987,767; 5,109,691; 5,345,809; 5,465,607; and 5,585,575.

SUMMARY OF THE INVENTION

The US Postal Service has no reliable manner of determining if anthrax, or other hazardous materials, are contaminating items of mail. It is desirable to do this before mail enters sorting and distribution centers. The present invention provides a system and method for detecting hazardous materials in or on mail.

The present invention is a system and method for detecting contaminants in and around objects, including mail pieces and parcels, and may include neutralizing the environment containing the contaminants or the contaminants themselves. The system of the present invention may include, but is not limited to, a housing such as a cabinet, a perforated container or surface, an air duct subsystem, a power subsystem, a sensor subsystem, an indicator subsystem, and a controller. Optionally, the system of the present invention can include a blower subsystem and a neutralization subsystem.

The housing creates an enclosure and forms an airflow barrier between the enclosure and the outside ambient air. The housing has a housing opening for inserting and removing the object(s). When there is a container, it forms a cavity for holding the object(s). The container has a shell with a plurality of perforations, or may be made of wire in which case there are already openings, and it is rotatably mounted within the housing. The container has at least one container opening for inserting and removing the object(s). When there is a surface with openings, the objects are supported by the surface. The power subsystem, operably connected to the container, rotates the container, or shakes or agitates or vibrates the surface.

The sensor subsystem tests an air stream for contaminants. The indicator subsystem is operably connected to the sensor subsystem and provides a signal when at least one contaminant is detected.

The air duct subsystem is capable of ducting the air stream to an appropriate place within the system. In one embodiment, the air duct subsystem can duct the air stream into a perforated pipe that is mounted within the container or adjacent to the perforated surface. The perforated pipe allows the air stream to enter in one case the cavity and in the other case perforations in the surface and the perforations allow the air stream to flow through and about the articles. The air duct subsystem can receive the air stream from the enclosure and/or adjacent the perforated surface and can duct it past the sensor subsystem, optionally forced by the blower subsystem.

Current devices that could detect and safeguard against biological agents can present further problems such as introducing additional contaminants into the air sample that may cause false alarms or shorten the life span of contaminant detection devices. Some current devices are deficient in that they allow the migration of deadly contaminants to the outside environment, or they require the use of costly high efficiency particle air filters (HEPA) filters to process air before release to the outside environment.

In one type of arrangement, the unit is self-contained and is a closed loop system in which the air is recirculated and not allowed to enter the ambient atmosphere. In such a system a HEPA filter is not needed.

The air duct subsystem is capable of ducting the air stream in a closed loop throughout the system. The air duct subsystem can duct the air stream into a perforated pipe that is mounted within the container. The perforated pipe allows the air stream to enter the cavity, and the perforation(s) in the cavity allows the air stream to enter the enclosure. The air duct subsystem can receive the air stream from the enclosure and can duct it past the sensor subsystem and back through the housing into the container, optionally forced by the blower subsystem.

In another type of arrangement, the air is filtered and then released to the atmosphere.

In another embodiment, there are air inlet and outlet openings in the container which permit air to enter and to leave.

The controller sequences operations among the sensor subsystem and the power subsystem so that particles that can be emitted while the object(s) are being tumbled within the cavity when the container is rotating. The particles can pass through the perforation(s) in the container from the cavity to the housing and then are entrained with the air stream into the air duct subsystem. The air stream and particles exit the housing and are ducted past the sensor subsystem which sends a signal to the indicator subsystem if contaminant(s) is detected in the particles.

Optionally, the blower subsystem can force the air stream through the air duct subsystem. If a blower subsystem is used to force the air stream, the controller can sequence activities among the blower subsystem, the sensor subsystem, and the power subsystem. Also optionally, when contaminant(s) is detected, a neutralization mechanism can inject a conventional contaminant neutralizer such as chlorine-calcium, formalin, or lye solutions into the air stream in the air duct subsystem. If a neutralization mechanism is used, the controller can sequence activities among the neutralization mechanism, the sensor subsystem, and the power subsystem, and optionally the blower subsystem.

The method of the present invention includes the steps of loading a perforated container or surface with at least one object, enclosing the perforated container or surface within a housing, and sealing the housing. In this method, the step of sealing forms an ambient air barrier which prevents air and particles emitted from the perforated container or surface into the housing from entering the ambient air outside the housing. The method of the present invention further includes the step of rotating the perforated container or vibrating the perforated surface. Rotation of the perforated container that contains objects can serve to release particles that are on and in the objects within the perforated container into an air stream that entrains emitted particles. It also includes, in another embodiment, the step of vibrating the perforated surface to release hazardous particles that are on and in the objects within the housing. The method further includes the step of sampling the air stream that enters the housing through the perforations in the container or surface. The method includes the steps of testing for at least one contaminant and providing an indicator if at least one contaminant is detected. The method can optionally include the steps of forcing air into the rotating perforated container, which in turn is forced through the perforations into the housing or forcing air in the vicinity of the perforated vibrating surface, and introducing a neutralizing agent into the air stream if the air stream contains at least one contaminant.

The container is not filled to capacity so as to allow room for the mail to "waterfall" during rotation. The speed may be adjustable so that the mail can tumble and collide. If desired, this can be made variable using software based upon the load that is sensed by sensors which are a part of the system using such software.

In one type of system air flow is established within a container to sweep hazardous particles that are entrained in the interior air and dislodge particles from surfaces therein and sweep the particles into a sensor unit for analysis. A container may be provided with at least one wall surface, which, in one embodiment, is the floor surface, as an air distribution plenum with air-flow holes or openings therein to allow the establishment of an air flow path within the container.

During the time that the air flow pattern is established, a hazardous-materials detection sensor or sensor system is located at or otherwise introduced into the air flow pattern, preferably at or downstream of the air exit port, for a sufficient period of time to sample the flow for a plurality of undesired or hazardous materials.

The distribution plate or surface defines an air distribution plenum therebeneath and includes a plurality of holes distributed across its surface. The air flow pattern can be established by an air-moving fan located within the container or by an auxiliary piece of equipment that connects to the container through an air inlet port and air outlet port to establish a desired air recirculation flow for some period of time. Once the flow has been established, a sensor or sensors are located within the exhaust flow for some period of time sufficient to effect the detection of any undesired or hazardous materials.

The present invention advantageously provides a system and method for quickly and efficiently detecting hazardous materials inside housings while the shipped materials are contained and prior to the unloading of the housing and possible dissemination/distribution of any hazardous materials.

Other features and advantages will be apparent from the following detailed description of preferred embodiments taken in conjunction with the accompanying drawings.

BRIEF DESCRIPTION OF THE DRAWINGS

FIG. 12 is a schematic isometric view of a rotating cage embodiment.

FIG. 13 is a schematic isometric view of a vibrating surface embodiment.

FIG. 14 is a schematic isometric view similar to that of FIG. 13, but where the surface is irregular.

DESCRIPTION OF THE PREFERRED EMBODIMENTS OF THE INVENTION

Previous attempts to detect hazardous materials in mail integrated the liberation device with the detection device. The present invention separates the two processes and incorporates multiple liberation modules to produce a flow of "free from contaminant" mail available for sorting. This logistic method decreases cost of detection through multi-module application of the detection instrumentation and also allows technology refreshing of instrumentation while maintaining the liberation hardware. Implementing this disclosure eliminates decontamination of sorting machinery, equipment or process, in that, contaminated mail never reaches those devices.

Figure 11:
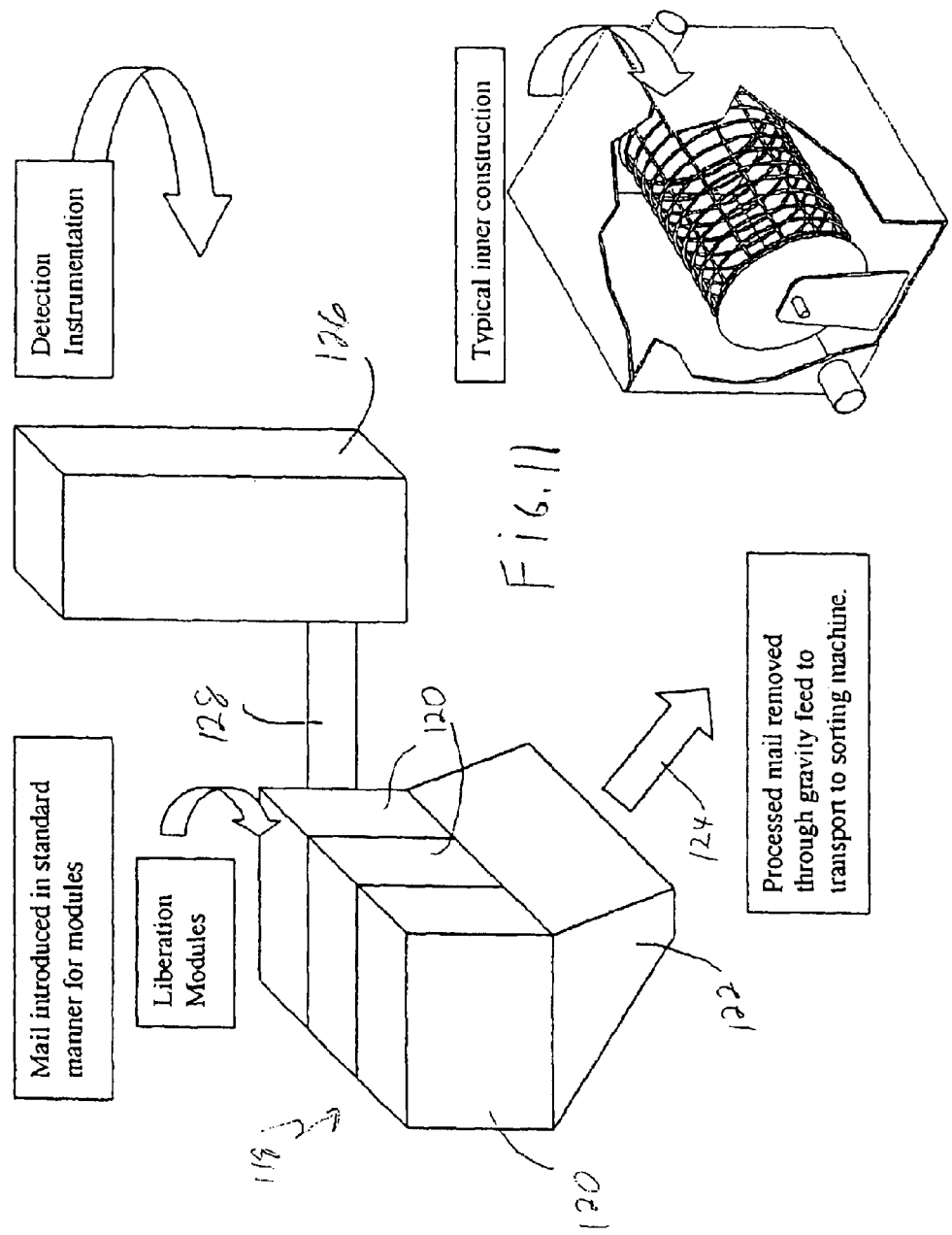
FIG. 11 is a schematic isometric view of a system for detecting hazardous material which is located upstream from the usual mail sorting/transporting system, and shows a ganged system.

FIG. 11 shows such a system schematically. It includes a bank 118 of modules for detecting hazardous material in mail. Each component 120 of the module provides a separate housing for processing batches of mail to assure they are free of hazardous material before they are released into the sorting system. The module 118 has an exit chamber 122 into which mail is delivered when it is determined that hazardous materials are not present. The arrow 124 indicates a means of delivering the mail from the module to the sorting apparatus.

There is also a bank of detection instrumentation 126, which may, if desired, also include apparatus for neutralizing the hazardous material. A schematic showing of a bus of electric or signal wiring and air ducting 128 is connected between the module 118 and the instrumentation/neutralization unit 126.

Figure 1:
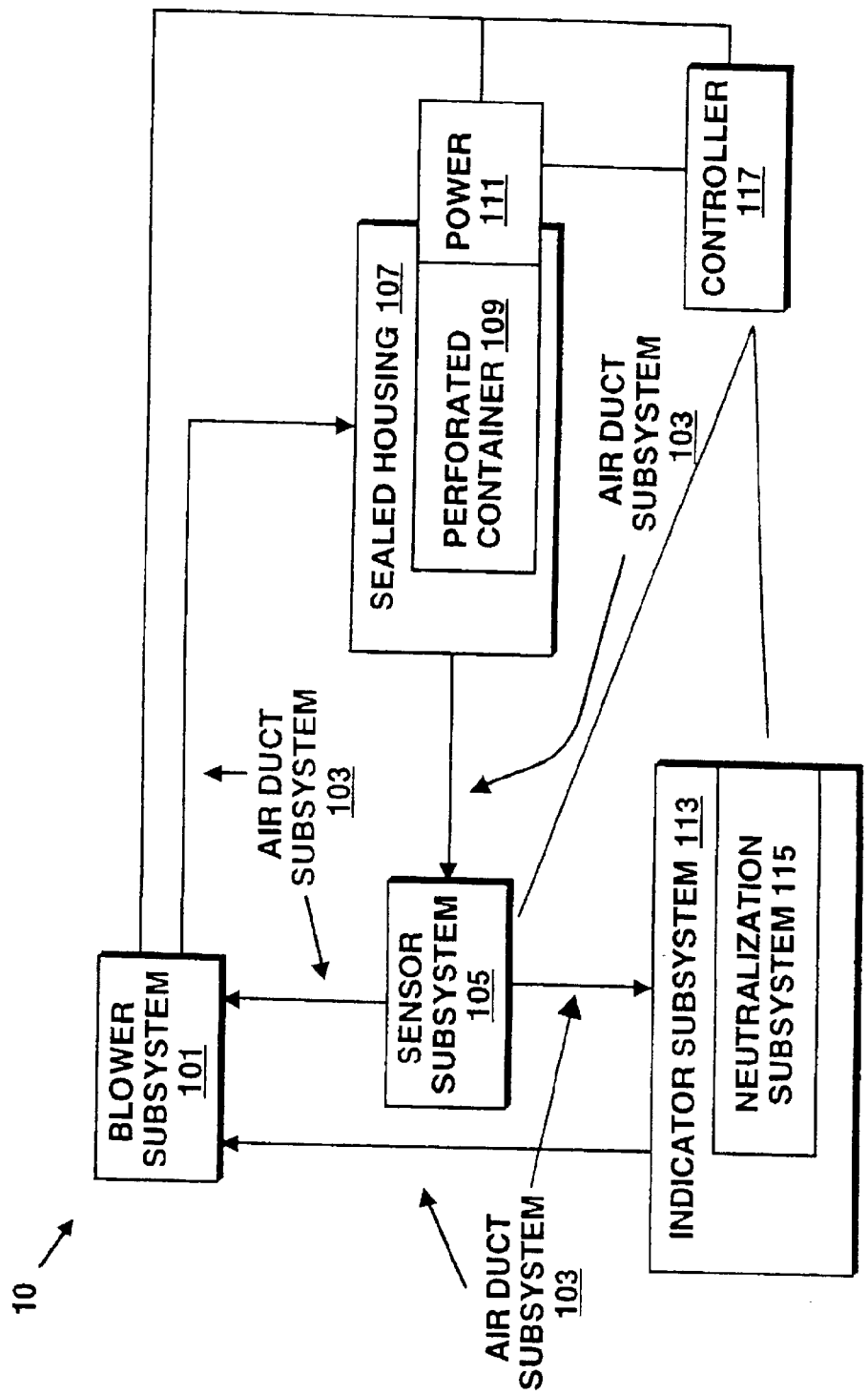
FIG. 1 is a schematic block diagram of the components of the system of the present invention.

System 10 of the present invention, shown diagrammatically in FIG. 1, includes, but is not limited to, a sealed or sealable housing 107 forming an enclosure, the enclosure containing a perforated container 109 forming a chamber or cavity, a sensor subsystem 105, and an indicator subsystem 113. Optionally, system 10 can include a blower subsystem 101. Components 101, 105, and 107 are in airflow communication through air duct subsystem 103. In addition, a power subsystem 111, an optional neutralization subsystem 115, and a controller 117 complete system 10.

In operation, perforated container 109 is rotated by power subsystem 111 while optional blower subsystem 101 forces an air stream through air duct subsystem 103. When perforated container 109 is loaded with objects, such as mail pieces and/or parcels, and rotated, any loose particles that are on or in the objects can be released and entrained in the air stream. These particles can eventually be forced into the enclosure formed by the sealed housing 107 through the perforations in perforated container 109 by the pressure of air flowing into the perforated container 109 and by the centrifugal force generated within the container. The particles can then be entrained into the air stream that is flowing into sealed housing 107 from the perforations in perforated container 109. This air stream is ducted by the air duct subsystem 103 past sensor subsystem 105 where it is tested by conventional sensor equipment, such as, for a nonlimiting example, the BIONI or Biological Aerosol Real Time Sensors manufactured by Pacific Scientific Instruments and the Biological Aerosol Warning Systems I, developed by the assignee of this application, or any cost-effective, real-time sensor for airborne biological particles or other contaminants. If contaminants are detected, indicator subsystem 113 provides an indication of the presence of contaminants. Optionally, neutralization subsystem 115 can operate cooperatively with the sensor subsystem 105 to neutralize contaminants in the air stream and also to neutralize contaminants in or on the objects bearing the contaminants. Controller 117 can sequence operations among the various subsystems, for example, activation and deactivation of the blower subsystem 101 and the power subsystem 111.

Figure 2A:
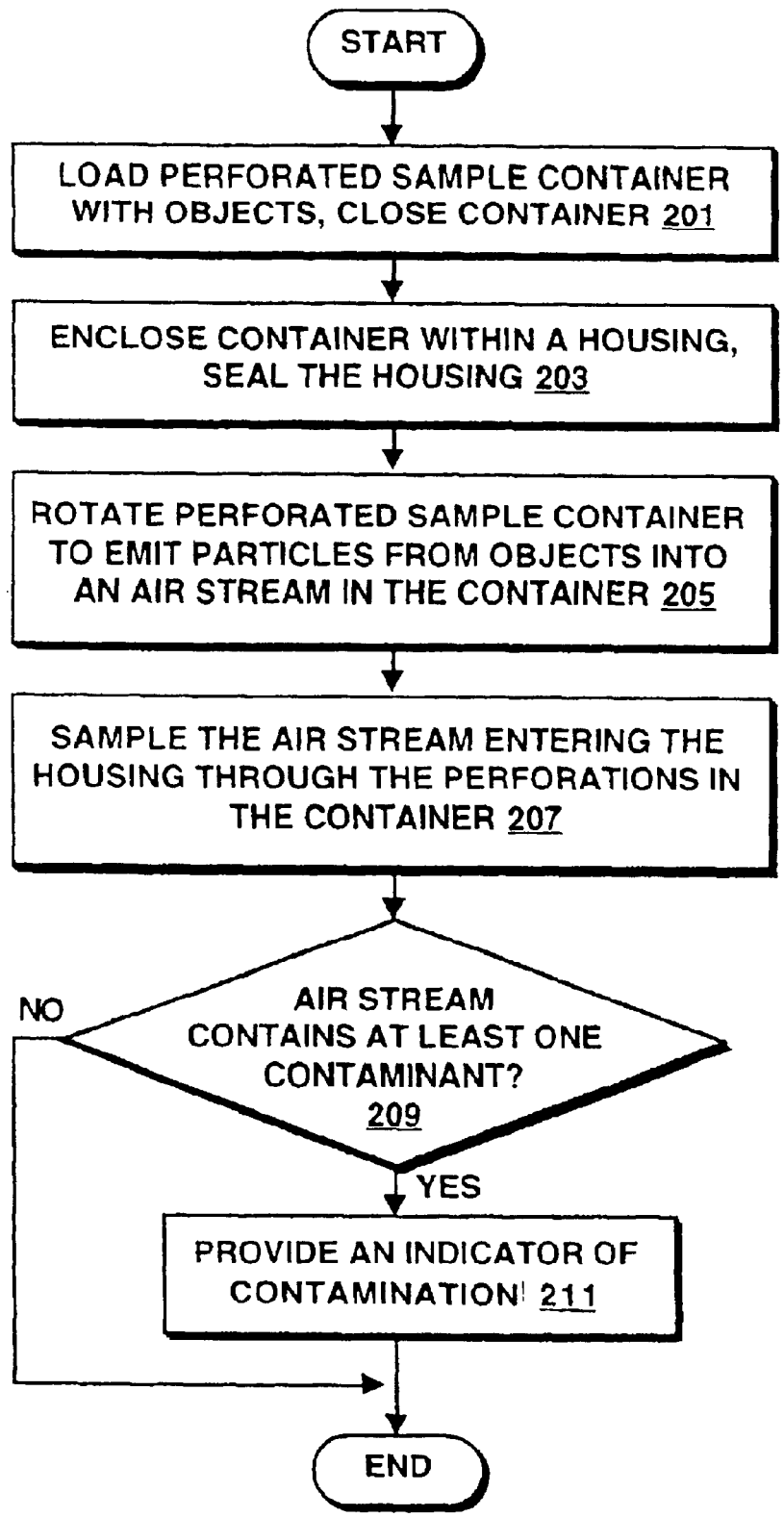
FIGS. 2A and 2B are flowcharts of the method of an embodiment of the present invention.

Referring now to FIG. 2A, one of the methods of the present invention includes the step of loading a perforated container with objects and closing the container (method step 201). This method further includes the steps of enclosing the perforated container within a housing and sealing the housing to prevent gas exchange between the air inside the housing and the air outside the housing (method step 203). This method next includes the step of rotating the perforated container and the objects within the perforated container so that any particles that might on or in the objects are shaken loose by the rotation and emitted into an air stream surrounding the objects within the container (method step 205). The method further includes the steps of sampling the air stream by the sensors for the presence of contaminants (method step 207), the decision step of determining whether the air stream contains at least one contaminant (decision step 109), and setting an indicator if at least one contaminant is detected (method step 211).

Figure 2B:
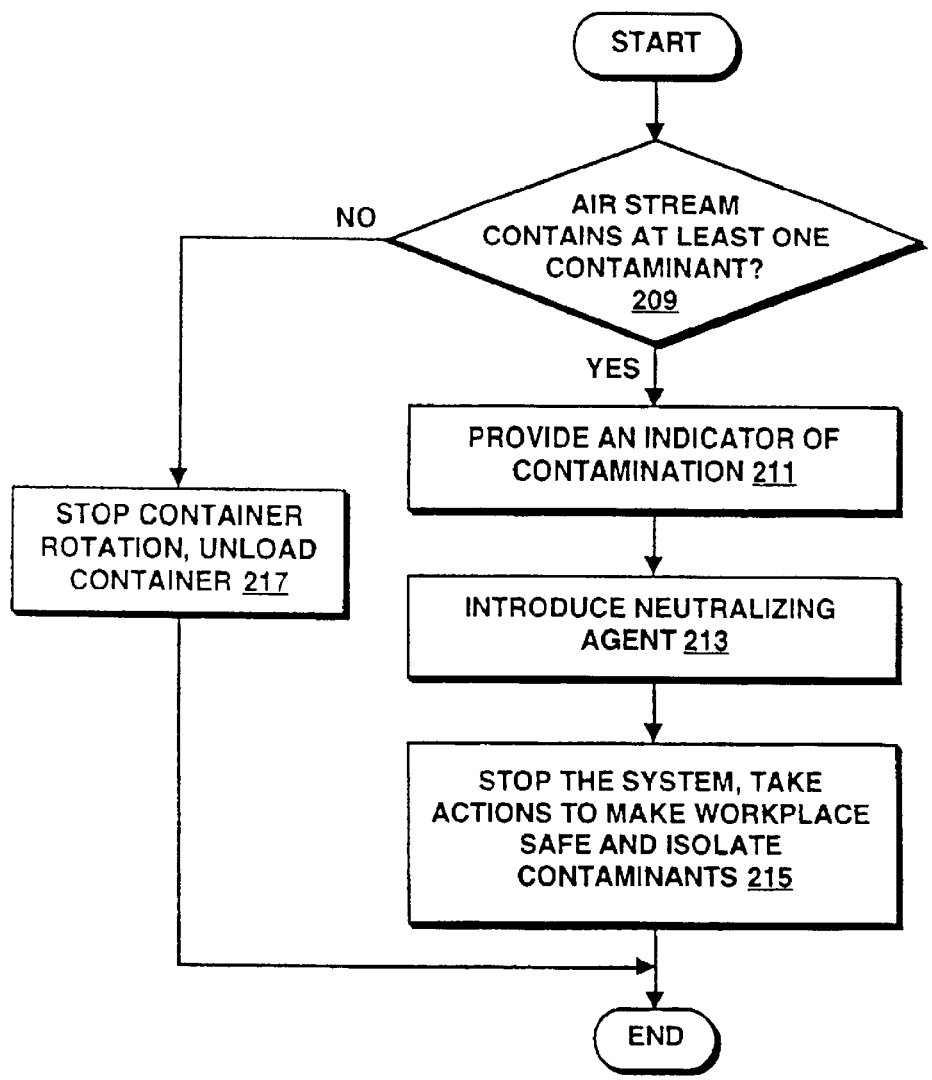

Referring now to FIG. 2B optional steps that can be taken if the air stream contains contaminant(s) include introducing a conventional neutralizing agent into the air stream if at least one active contaminant is detected (method step 213) to neutralize the air stream. The neutralizing agent is also used on the objects from which the contaminants were detected. The method includes the further step of stopping the system and taking actions to make the workplace safe and to isolate contaminated objects (method step 215). If the air stream is found to be free of contaminants, the method of the present invention includes the steps of stopping and unloading the perforated container (method step 217).

Figure 3:
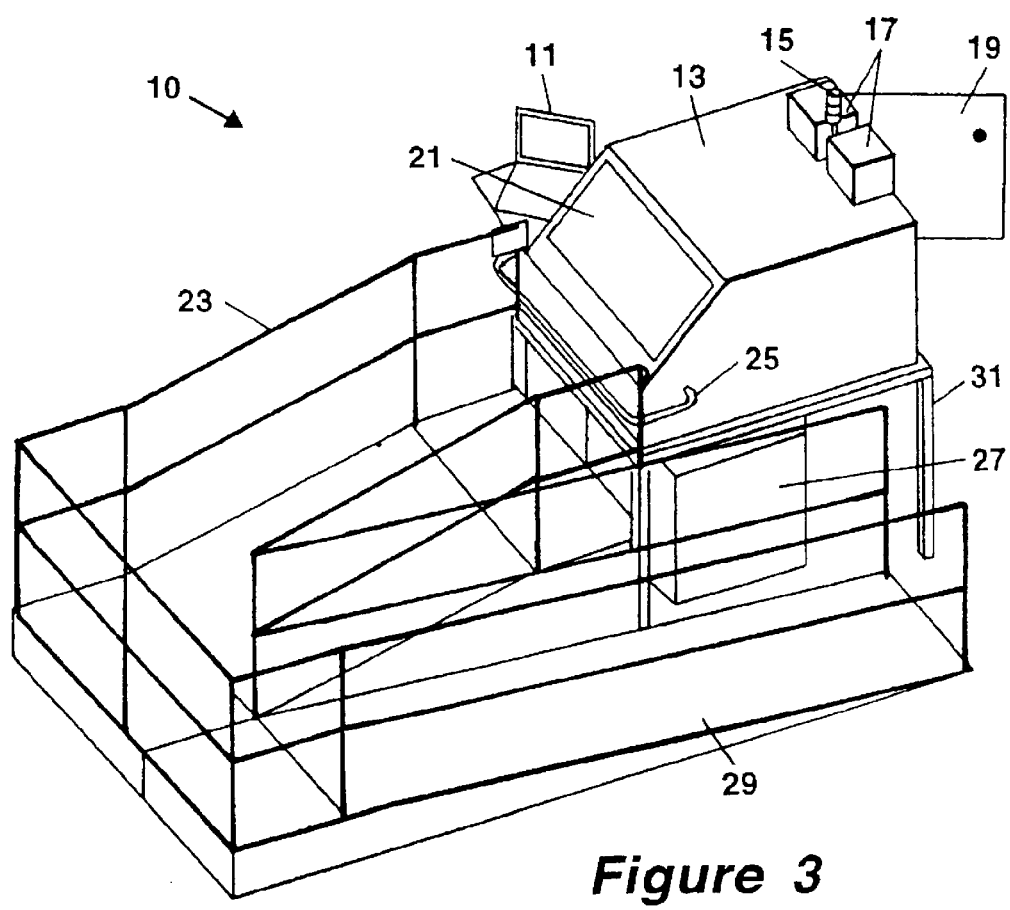
FIG. 3 is an isometric view of an embodiment of the system of the present invention.

Referring now to FIG. 3, system 10 of this embodiment of the present invention includes housing 13, mounted on housing stand 31, and having a housing lid 21, capable of being opened. In this embodiment, the housing can be, for a nonlimiting example, predominately 16–18 gauge stainless steel or any material to allow for corrosion resistance and internal sanitization if necessary. An external framework of powder-coated steel or any other type of material can be used for supporting the housing. The housing can be any size, and could be specially constructed to accommodate certain sizes of objects or areas of application. For example, if the system is to be used primarily in a mailroom, that application could require a relatively large housing to accommodate packages that might be entering the mailroom. On the other hand, if the system were primarily for home use, the housing could be quite small, if desired, to accommodate analysis of flat letters only, for example.

Figure 6:
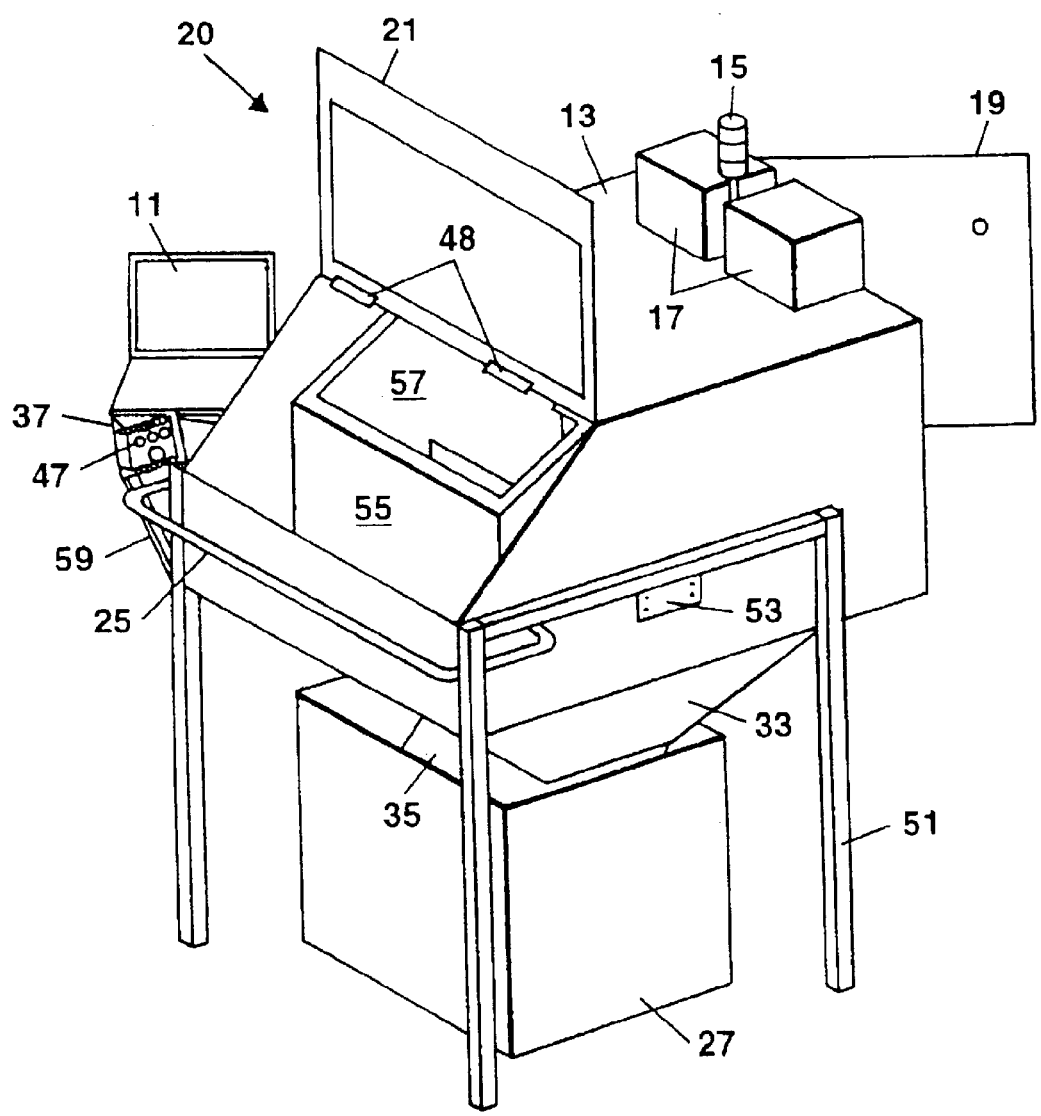
FIG. 6 is an isometric view of a front view of the open housing and container of another embodiment of the housing stand of the present invention.

The housing lid 21 is preferably, although not necessarily, a lift-open glass door operably connected to the housing 13 by lid hinges 48 (shown in FIG. 6). System 10 also includes conventional sensors 17 which are, in this embodiment, a particle sensor and a biological agents sensor, the complementary action of which enhances contaminant detection possibilities. The particle sensing system, illustratively the BAWS I system, is specially suited to detect particles in the 2–10 micron range favored for aerosol dispersion of biologic agents. The biological agents sensor, illustratively the BAWS III sensor, utilizes ultra-violet laser fluorescence technology to analyze captured particles for the presence of biological agents. In this embodiment, the two sensors can be coupled together by an RS-232 communications line, or any other appropriate electronic communications mechanism. The particle sensor can communicate with a controller 11 through an RF link to the RF radio network or any other suitable means of wired or wireless electronic communications. Any sensors, including but not limited to chemical, biological, and particle, can be used in the system of the present invention.

Figure 5:
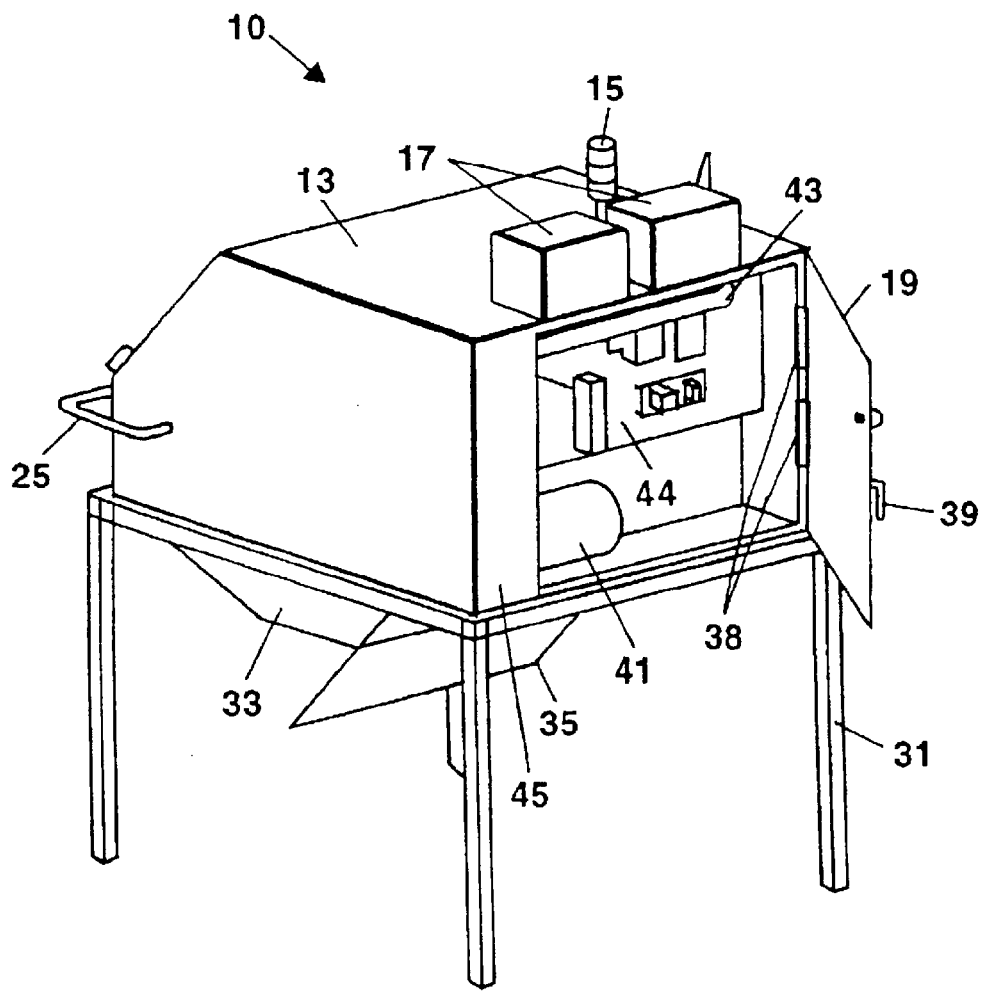
FIG. 5 is an isometric view of a rear view of an embodiment of the system of the present invention.

Controller 11, which can be a personal computer, a programmable logic controller, or other such device, is operably connected to interface panel 44 (shown in FIG. 5). In this embodiment, controller 11 is a personal computer with a Universal Interface Unit for connecting external sensors and an RF network radio. The personal computer of this embodiment operates under any operating system that supports the appropriate hardware and software to interface with and control the various components of the system. Application software to control system 10 is standard BAWS sensor software with upgrades as follows: (1) a new communications message format is added to accommodate information from the sensors of system 10, and (2) the software is modified for non-military use. Any application software appropriate for the sensors selected for the system can be used.

Figure 4:
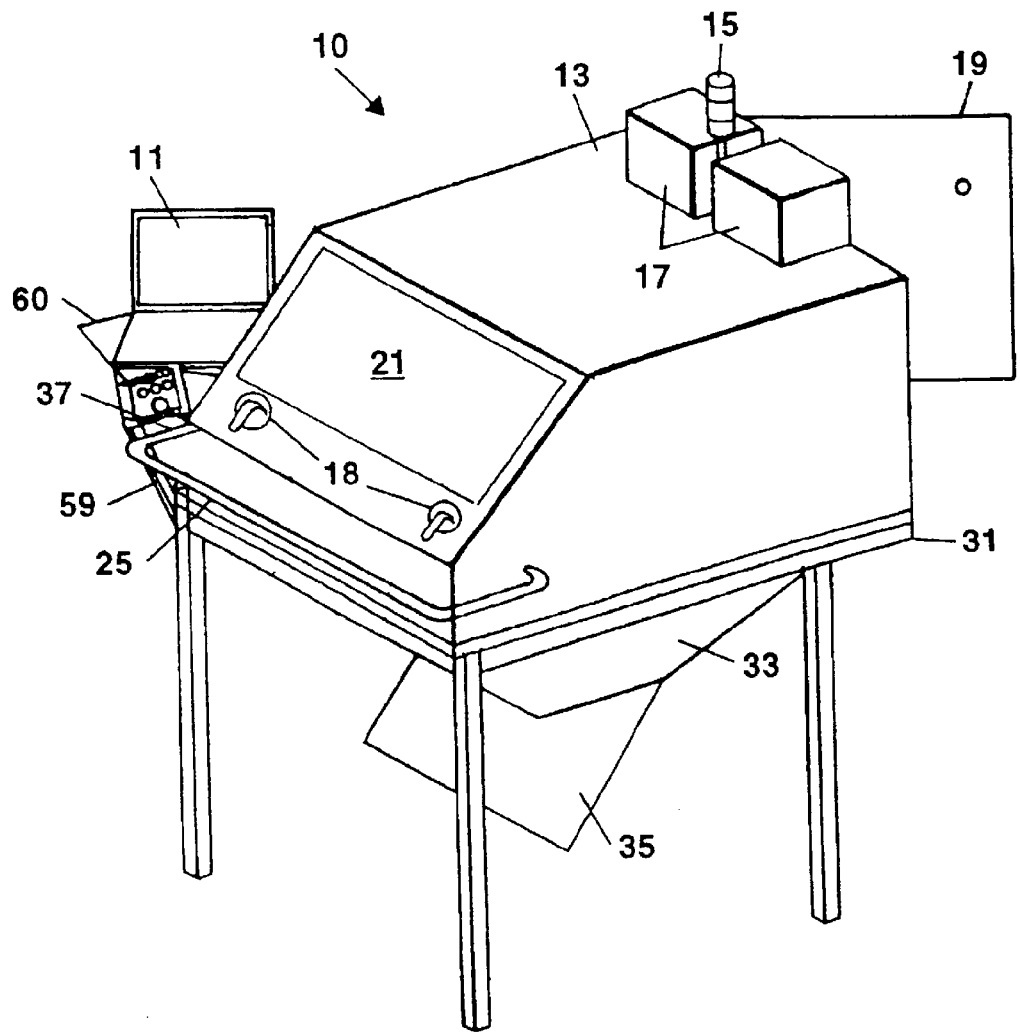
FIG. 4 is an isometric view of a front view of an embodiment of the system of the present invention.

System 10 can also contain a visual indicator 15, which is an embodiment of the indicator subsystem 113, that can be color-coded to indicate contamination states. System 10 also includes a rear housing door 19 through which the operator can access the interface panel 44, but which does not allow gas exchange with the air-sealed environment of the housing 13. System 10 also can optionally include discharge handle 25 and discharge receptacle 27. (When used in a mail system, the receptacle can be any of the receptacle types presently used in mail systems.) Discharge handle 25 can be pressured manually to release objects from the container 55 (shown in FIG. 6) and housing 13 into discharge container 27, which can be any container suitable for the weight and size of the objects being tumbled in container 55. The handle 25 and housing 13 are operably connected by an interlocking conventional mechanical linkage having a conventional camming feature that reliably seals the discharge hatch lid 35 (FIG. 4). The conventional interlocking mechanism insures that the housing 13 is incapable of being opened during use. It is envisioned that this could be used manually or could be operated by the control system and could a pneumatically- or electrically- or hydraulically-controlled, so manual intervention is required. In this embodiment, an optional loading ramp 29 is shown, having ramp rails 23 and leading to the housing 13. The loading ramp 29 can aid in transporting objects to and loading objects into housing 13.

Referring primarily now to FIG. 4, the front of the housing 13, housing stand 31 and controller 11 is shown. In this embodiment, controller stand 60, mounted on controller shelf support 59, is operably connected to housing 13 and housing stand 31. Controller 11 can be located any distance from housing 13, but must have electronic (wired or wireless) connection with interface board 44 (shown in FIG. 5). Also shown is control panel 37 which, in this embodiment, is a panel with start, stop, load/unload, and emergency stop buttons. Also shown are housing lid latches 18 that insure that the housing is sealed against gas exchange with the ambient workspace. Also shown are housing recess 33 and housing discharge lid 35. Housing recess 33 is formed to allow free rotation of container 55 (see FIG. 6). Housing discharge lid 35 is operably connected to handle 25 such that when handle 25 is depressed, after housing discharge lid 35 is opened and the removable lid (not shown) is removed from container 55, container 55 rotates into discharge position and the objects within container 55 drop into receptacle 27.

Figure 8:
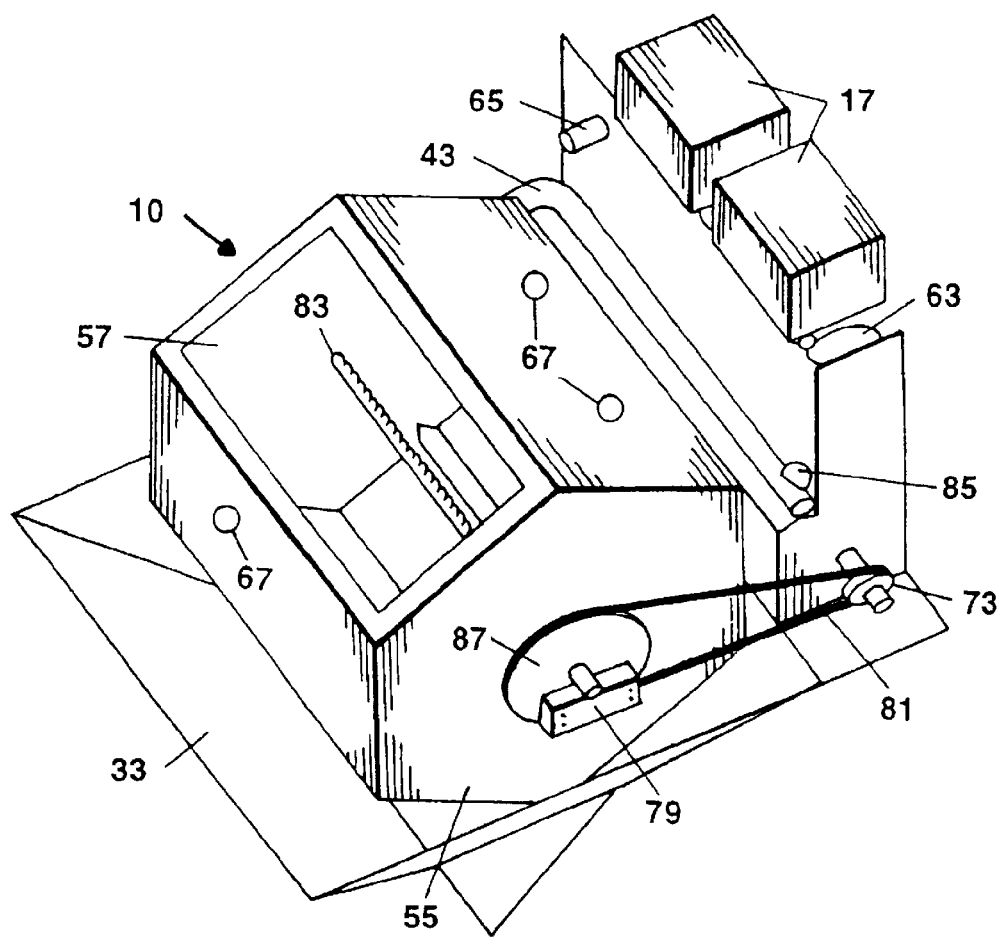
FIG. 8 is an isometric partial view, taken from the front, of the perforated container and interface board of an embodiment of the present invention.

FIG. 5 shows the rear of housing 13, housing stand 31, and interface panel 44. In this embodiment, interface panel 44 includes electronics to provide the interface between controller 11 and operational subsystems of the system of the present invention. For example, controller 11 allows the operator to stop the rotation of container 55 through a push-button on control panel 37. Interface panel 44 contains electronics to disable power to motor 41, which thus disables rotation of container 55 (the coupling of motor 41 to the rotation of container 55 is shown in FIG. 8).

Rear housing wall 45, along with interface panel 44, complete the rear sealed housing. Interface panel 44 is covered during operation by rear door 19 which can be operably connected to the housing 13 by rear hinges 38 and latched in place by latch 39. Shown also is a pipe of the air duct subsystem 43. This part of the piping ducts air from the housing 13 to the recirculation blower 63 (shown in FIG. 7). This embodiment recirculates the air which leaves the sensors back into the container so that air is not discharged into the atmosphere. However, in other embodiments, the air is not recirculated.

Figure 7:
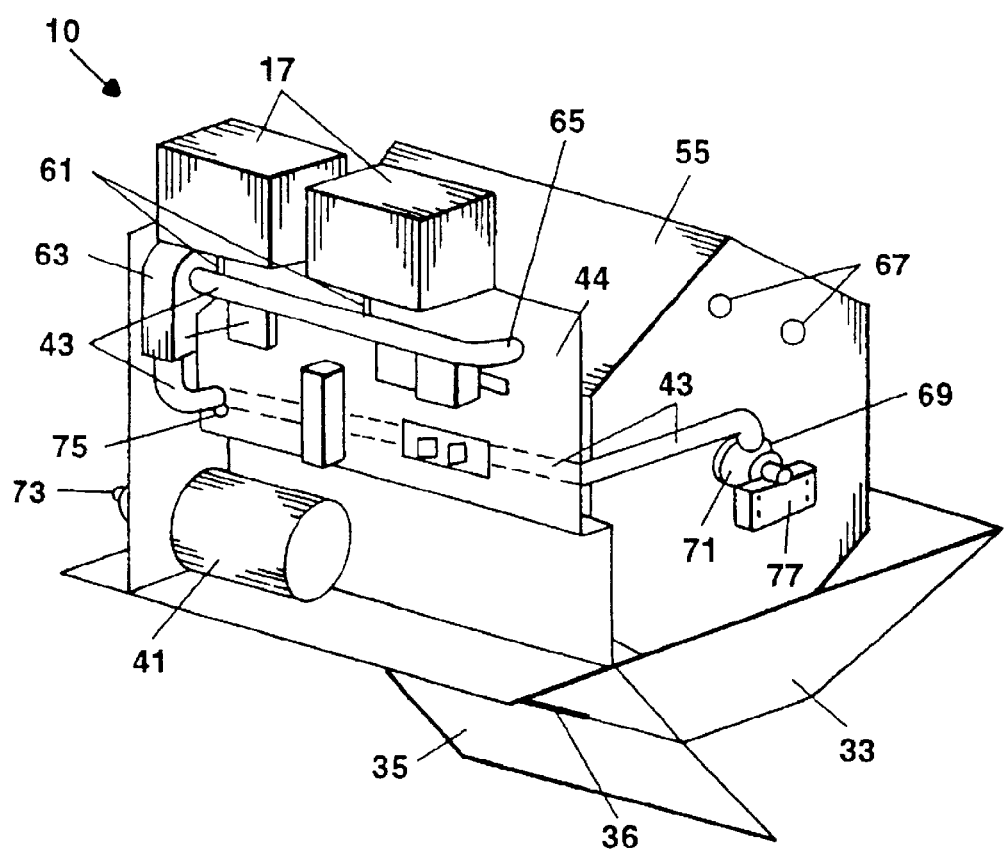
FIG. 7 is an isometric partial view, taken from the rear, of the interface board and perforated container within the housing of an embodiment of the present invention.
Figure 19:
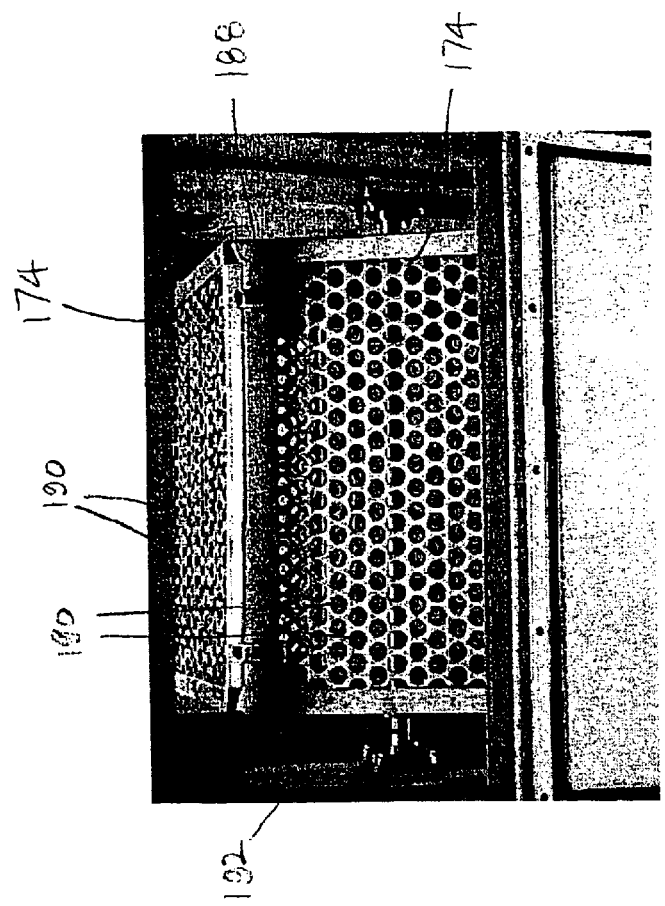
FIG. 19 is a view of a portion of the front of a hex basket rotating cage.

FIG. 6 shows another embodiment 20 of the system of the present invention which includes a housing stand in which the housing 13 is supported by attached legs 51 and housing support connectors 53. Also shown is the perforated container 55 and cavity 57. FIG. 7 provides a rear view of interface panel 44 and container 55, shown with the housing removed. Container 55, which can be any shape, is six-sided in this embodiment. Some further detail of this construction is shown in FIG. 19. It has a removable lid (not shown, attached conventionally when in place) which, when opened, can admit objects into container 55 to be tumbled. Once loaded, container 55, perforated with one or more perforations 67, can be rotated to tumble the objects and agitate them. While the perforations are only shown in the side of rotable container 55 in this figure, the perforations will generally be located on the periphery of the drum and not always on the sides. The preferred rate of rotation is sufficient to tumble the objects in container 55, but not so fast that the objects are pinned to the sides of container 55, thus preventing agitation. The air duct subsystem 43 directs an air stream at the objects within the container by means of a perforated air pipe 83 (shown in FIG. 8) that also acts as an axle for the rotating container 55. Air pipe 83 is in airflow communication with the air duct subsystem 43 which junctions with air pipe 83 at intersection 69. Rotating coupling 71 provides a rotatable connection between the air duct subsystem 43 and the container 55 by allowing the air stream to flow through the coupling 71 while one portion of the coupling 71 and the container 55 rotate. Container 55 is attached to housing 13 on one side by air duct housing mounting connection 77.

Motor sprocket 73 which drives, for example, a chain, belt, or direct drive, that acts as a container rotation means to rotate the container 55 is shown. Also shown is blower 63 which forces the air stream through the air duct subsystem 43. It can be seen that air leaving container 55 at exit port 65 passes sensor probes 61 on its way to recirculation blower 63. As long as power is supplied to the system, blower 63 forces the air stream back through interface panel 44 at air duct housing entry 75 and into container 55 at rotating coupling 71. If contamination is detected by conventional sensors 17 through air stream sampling by sensor probes 61, a signal is sent to the indicator subsystem and to controller 11 through interface panel 44.

Figure 15:
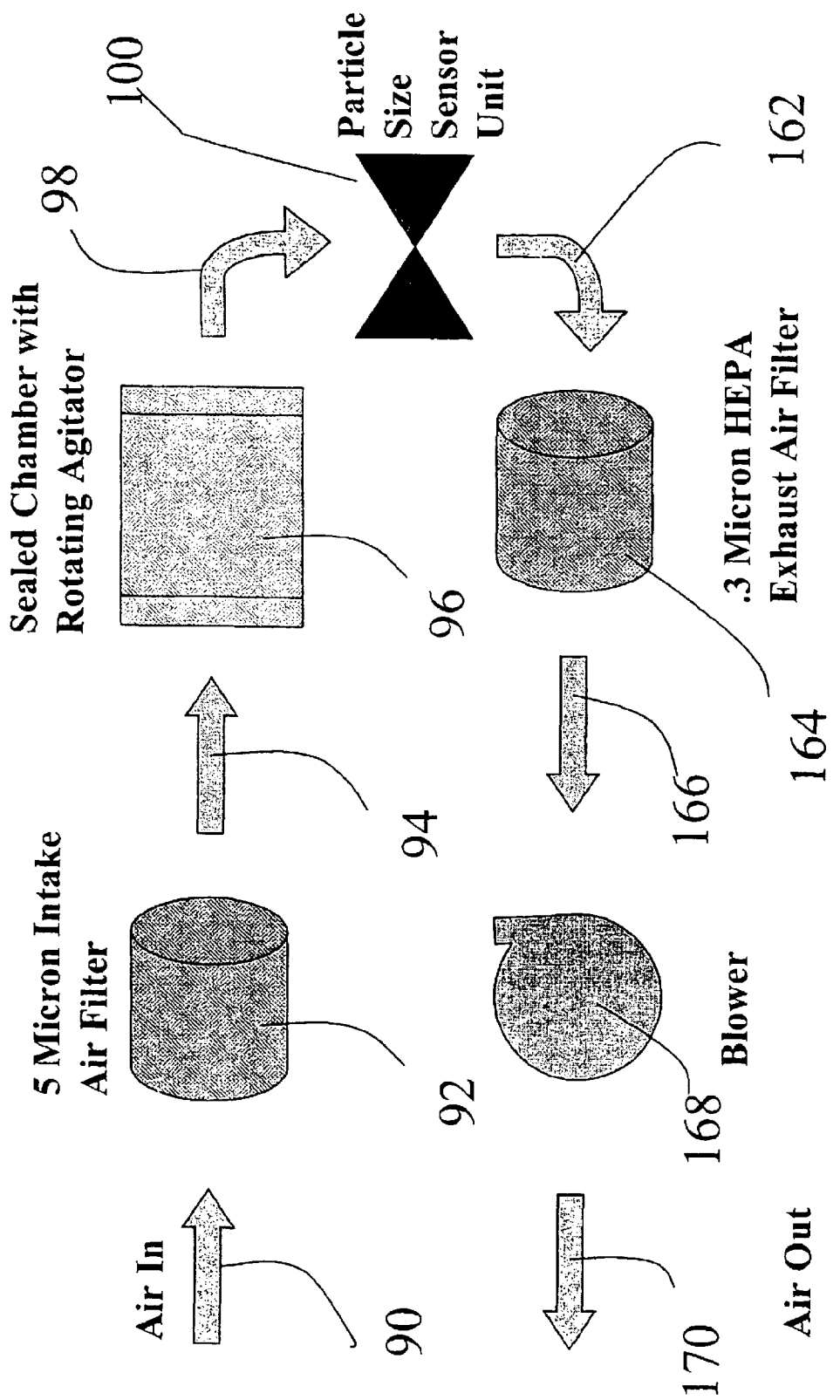
FIG. 15 is a diagrammatic view of another embodiment of the present invention.

FIG. 8 shows the front of container 55 with the housing removed. In this view, container sprocket 87 and chain or belt 81 are shown. Motor 41 (shown in FIG. 7) drives, and thus provides the rotation to motor sprocket 73 and thus drives chain 81 and container sprocket 87 to rotate container 55. Container 55 is connected to housing 13 on the motor side by chain or belt drive housing mounting connection 79. Air duct junction 85 is shown by which the air stream is provided by the blower 63 at air duct housing entry 75 (shown in FIG. 7). When recirculation is used, the requirement for a HEPA filter, as is used in the arrangement shown in FIG. 15, is eliminated.

Figure 9:
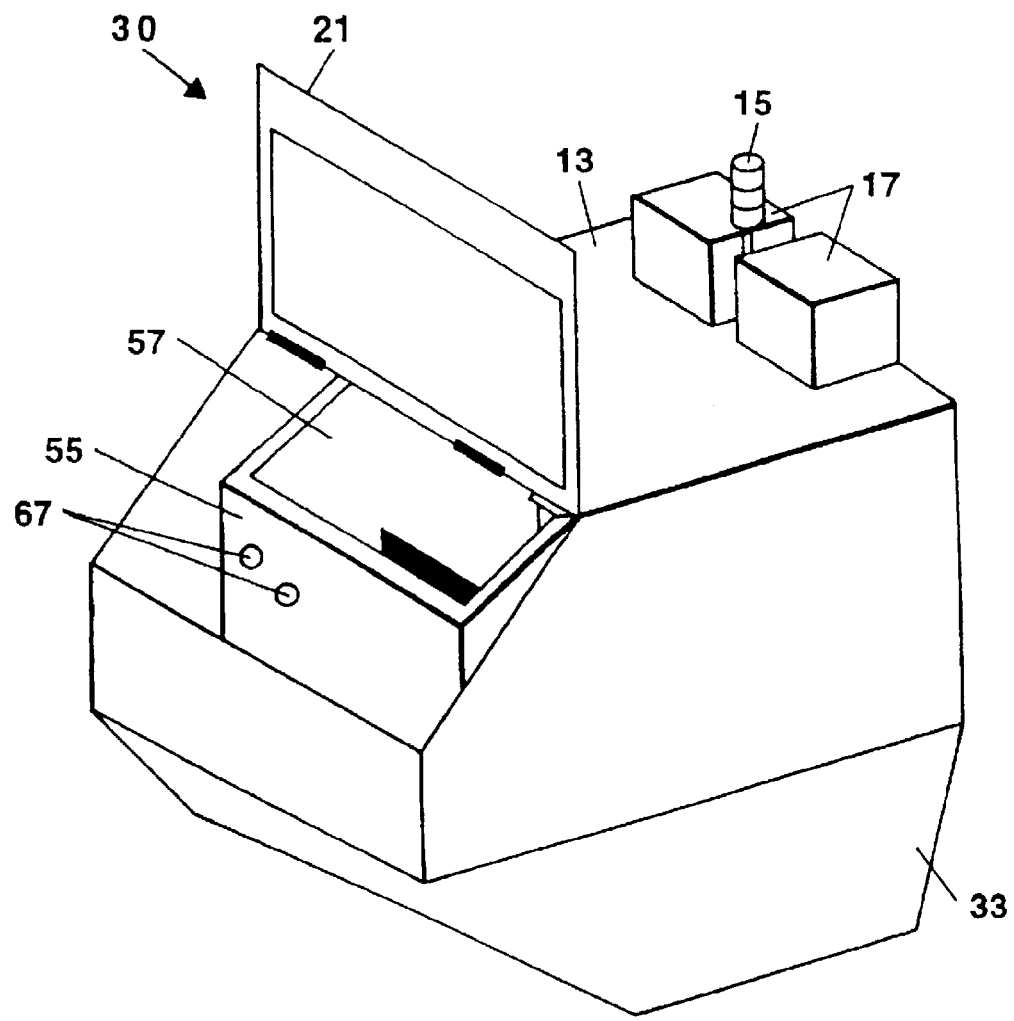
FIG. 9 is an isometric view of another embodiment of the present invention in which the sensors and indicator are directly sensing the air stream in the housing.

FIG. 9 shows a further embodiment 30 in which conventional sensors 17 directly sample air inside the recess 33 of housing 13 and provide a first signal to indicator 15 if at least one contaminant is detected. System 30 further includes drum or container 55, which is six-sided with perforations 67 in its periphery, the drum 55 defining cavity 57. Cavity 57 is loaded with objects and then closed as a lid (not shown) is positioned over the opening in container 55. After the objects are loaded, housing lid 21 is shut to prevent gas exchange between the air within housing 13 and the ambient air. Drum 55 is rotated by any kind of conventional power supply (not shown), thus tumbling the objects within cavity 57 and releasing particles associated with the objects into the air in the cavity 57. Air and particles mix and exit cavity 57 through perforations 67 into the enclosure formed by housing 13 where the air and particles are tested for contamination by conventional sensors 17.

Figure 10:
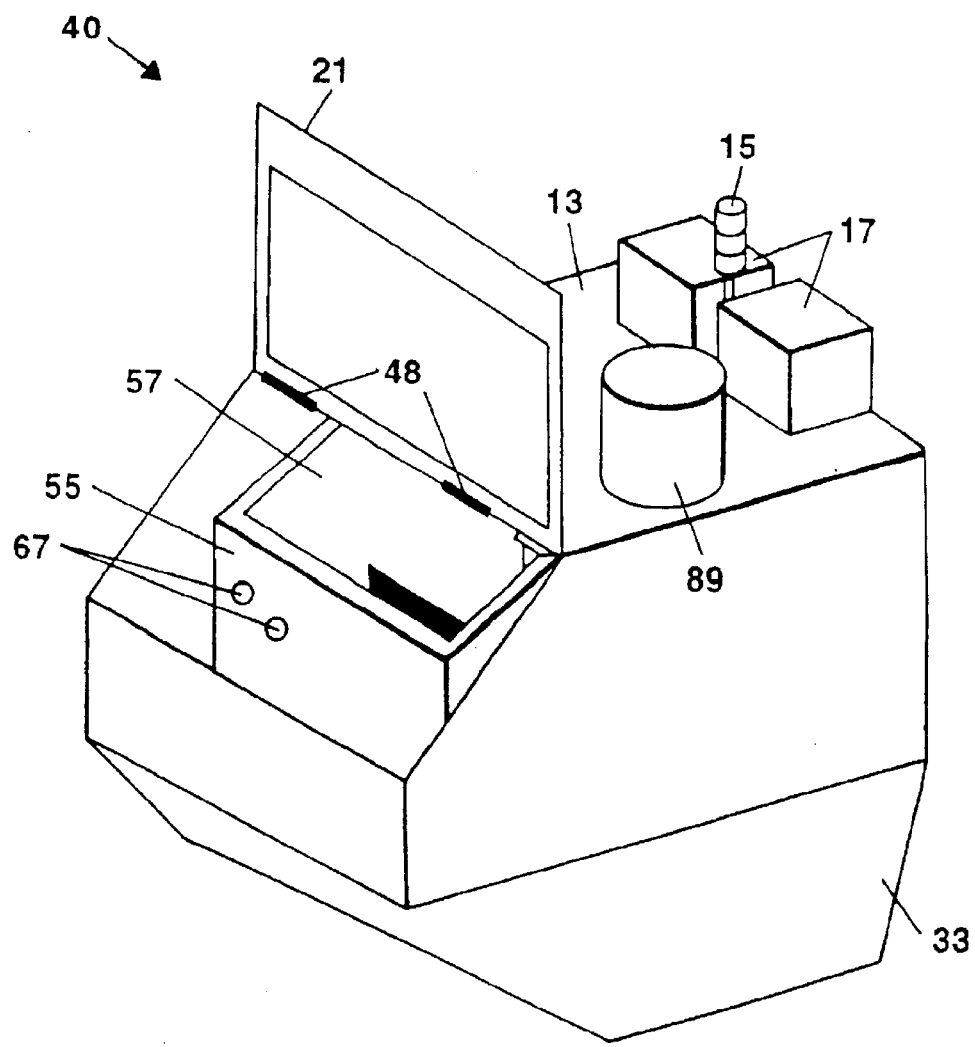
FIG. 10 is an isometric view of a further embodiment of the present invention in which the blower, sensors, and indicator, are blowing an air stream directly into the housing and directly sensing the air stream in the housing respectively.

FIG. 10, is a still further embodiment 40 which is the same as embodiment 30 except that a conventional blower 89, operably connected to housing 13, forces air into housing 13. The forced air can increase air circulation into container 55 and conventional sensors 17, thus potentially increasing the frequency and reliability of contaminant detection by conventional sensors 17.

Whereas some of the previous embodiments have related to a closed loop system, the embodiments to be described below are not usually used in a closed loop, although they could be modified to be closed loop systems.

FIG. 12 shows a rotatable cage embodiment in which a cage 142, which may be formed of a plurality of wires 130 to provide openings for the passage of air, but it could also be formed of a solid material which is provided with a plurality of openings. The cage 142 is mounted on an axle 132 which is rotatably mounted in bearings in standards 134. The cage 142 is rotated to provide agitation of the mail items to remove particulate matter from the inside or outside of the mail. The cage 142 is mounted in a housing 136 which has an air inlet 138 and an air outlet 140 so that when air is moved through the housing while the cage is rotating, it will entrain particulates of hazardous material and be carried by the air. Thus, when the air stream is provided, the particulates are entrained in the air stream and removed. The arrangement of air inlet and air outlet can be changed as and when desired. The air outlet 140 is connected via the duct 128 (FIG. 11) to the instrumentation where sensors determine whether or not hazardous material is present.

The housing 136 has an opening, closable by a door such as is shown in FIGS. 13 and 14, or as shown in FIGS. 3, 4, 6, 9 and 10.

Thus, in operation, a rotating perforated cylindrical cage is provided within a sealed container into which the suspect contaminated media is placed. The cylinder is rotated through a mechanical drive. The particulates are dislodged primarily through tumbling and secondarily through centrifugal force. Dislodge particles are entrained into an air stream and pass through a detector as described above.

FIG. 13 shows a housing 144 having a shaker surface 146 which is driven by shaker drivers 148, or a similar physical vibration source, attached to shallow box 150 mounted on a slight angle, approximately 20 degrees in this nonlimiting example, within the housing 144, the box 150 having openings 152 therein. The suspect contaminated media is contained in a hopper (not shown) located above the box 150 with the shaker drivers 148, and which feeds the mail into the housing 144 through an opening 154. This opening 154 may have a door of the type shown in some of the previous figures. The mail passes into the lower section of the housing 144 (or exit as indicated in FIG. 11) only by sliding over the shallow box 150 to the bottom of the chamber where the mail passes into the exit. The shaker table drivers 148 vibrate the box and liberate the particulates. Air flow caused by inlet 156 and outlet 158 from within the vibrating box carries away the particulates to the detector arrangement 126 as shown in FIG. 11.

FIG. 14 shows a variation of the FIG. 13 embodiment using a corrugated top surface 160 for the vibrating box 150 to aid in separation of the particulates from the suspect media moving over the box.

This allows the liberation of suspect particles through use of a rotating cage, or a vibrating surfaces with openings, to isolate the suspect particle detection prior to introduction to a document sorting process.

FIG. 15 is a diagrammatic view of the steps of the process that takes place with the apparatus of the present invention.

There are two types of rotating cage arrangements shown, although other arrangements are possible and these are just two nonlimiting examples. One type is a hex cage and the other is a basket cage. In one series of embodiments, the cages are in the form of baskets which are easy to be carried by a worker.

The operation proceeds generally as follows in one, nonlimiting example of an embodiment of the invention. Air enters 90 through an inlet and passes through a 5 micron intake air filter 92. The air flows 94 to a sealed chamber with a rotating agitator 96. The air then flows 98 to a sensor suite or particle size sensor unit 100. It leaves the suite 100 and flows 162 to a 0.3 micron HEPA exhaust air filter 164. The air exits the filter 164 and flows 166 to a blower 168, and then exits at 170.

Figure 16:
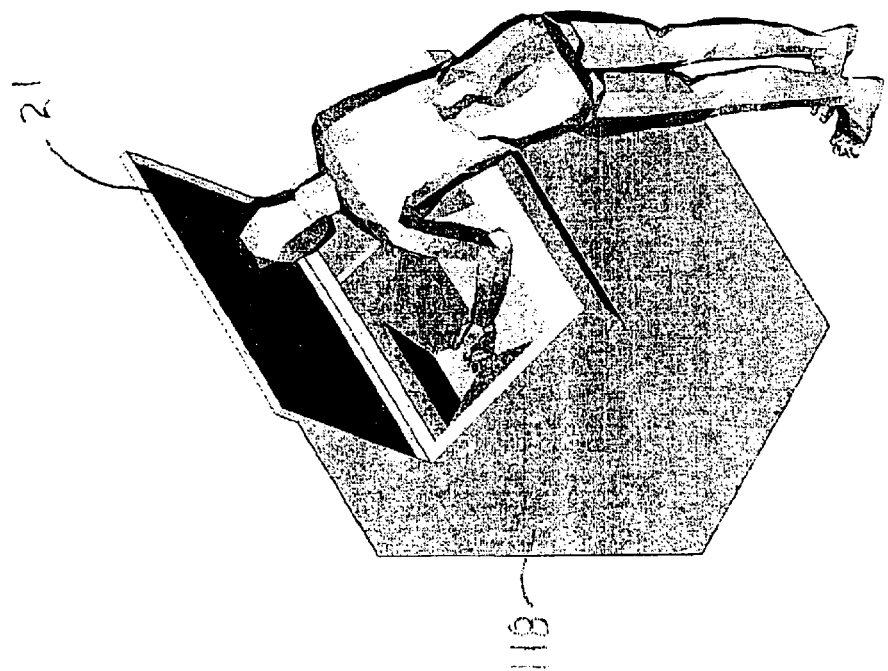
FIG. 16 is a schematic isometric view of a module being loaded with mail by a worker.
Figure 17:
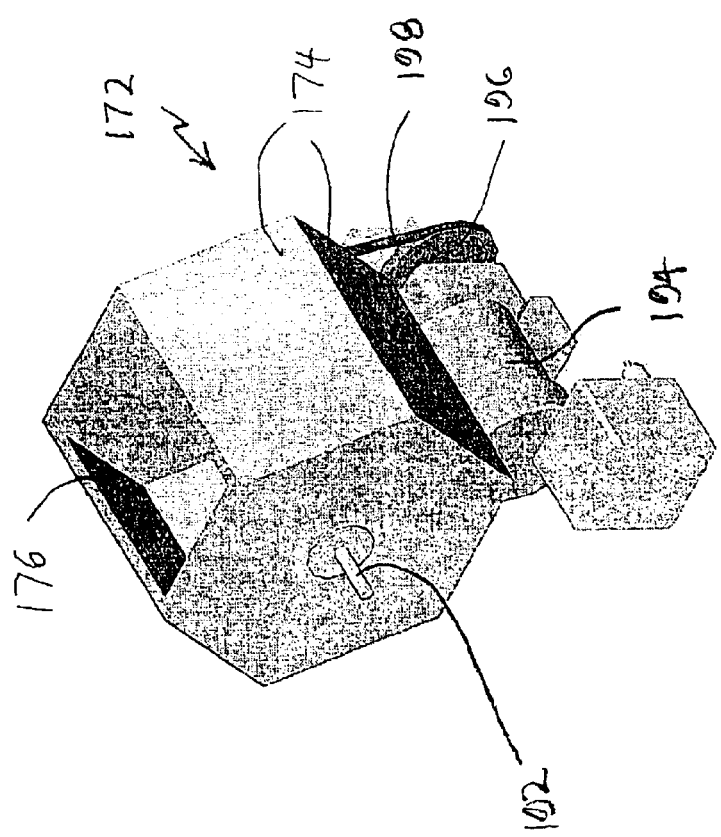
FIG. 17 is a schematic isometric view of a hex basket type rotating cage.

FIG. 16 is a schematic isometric view of a module 118 being loaded with mail by a worker into the module, the cage being a hex basket type rotating cage as shown in FIG. 17. The door 21 is shown in the open position.

FIG. 17 is a schematic isometric view of a hex basket type rotating cage 172. The basket has six sides 174, one of which has a loading and unloading opening 176. There is a door (not shown) for closing the cage before it begins rotating.

Figure 18:
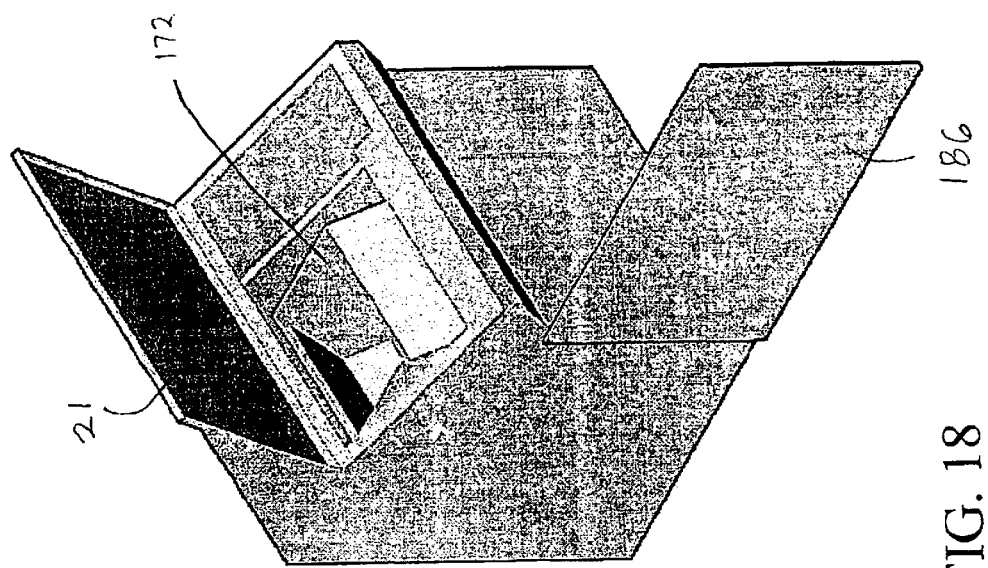
FIG. 18 is a housing for a hex basket rotating cage.

FIG. 18 is a housing 184 for the hex basket rotating cage 172. It has a front door 186 for access, as well as a loading and unloading door 21. The cage can be seen in place in its operating position.

FIG. 19 shows some details of the hex basket cage 172 including two of its sides 174 and a joint 188 where the adjacent sides are joined. The sides have perforations 190 and the cage is mounted on an axle 192 for rotating movement. The cage is driven by a motor 194 (FIG. 17) which drives a pulley 196 for driving a belt or chain 198 which drives a pulley (not shown) on the cage axle.

Figure 20:
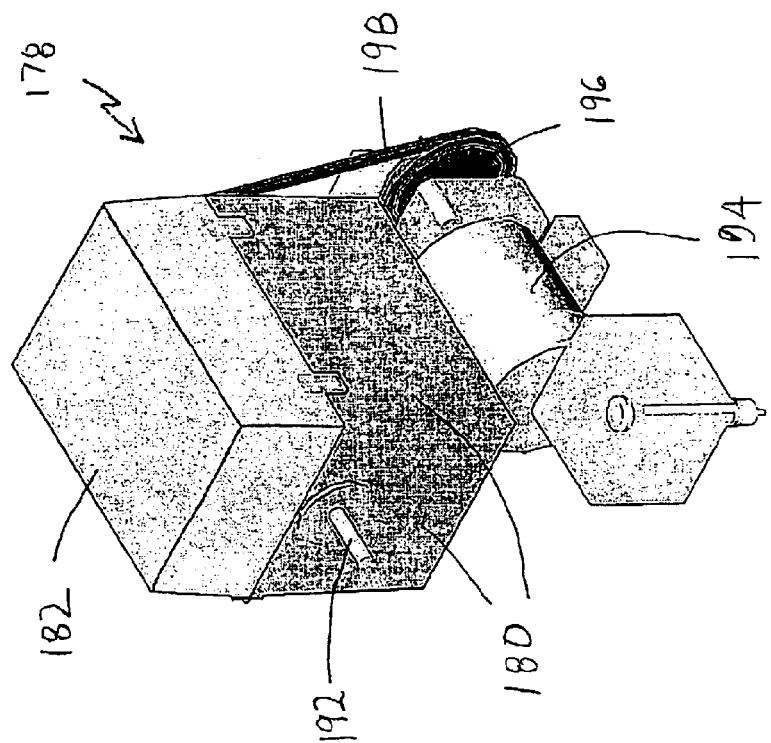
FIG. 20 is a tote basket rotating cage.

FIG. 20 is a schematic isometric view of a tote basket rotating cage 178. There are sides 180 which form the container and a hinged door 182 closes the cage when rotation is about to begin. The cage is driven in a similar manner to that described in connection with the hex basket cage 172 of FIG. 19.

Figure 21:
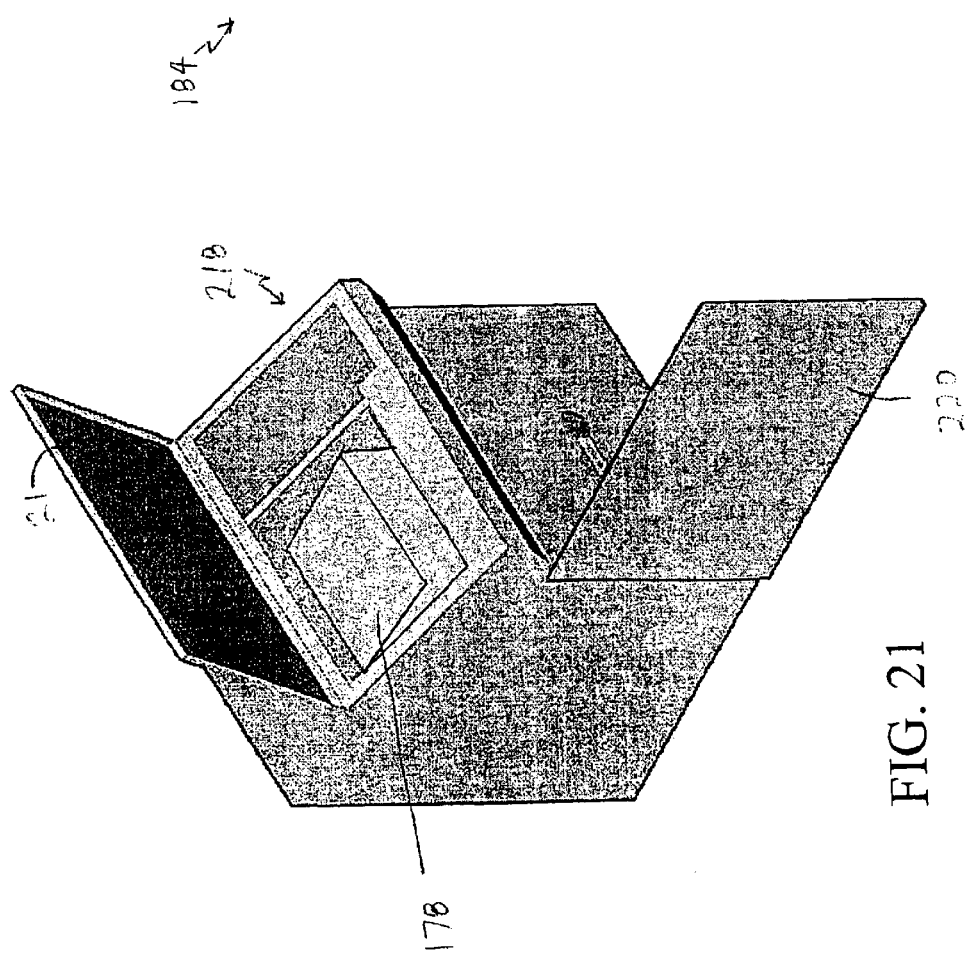
FIG. 21 is a housing for a tote basket rotating cage.

FIG. 21 is a housing 218 for a tote basket rotating cage 178. It has a front door 220 for access, as well as a loading and unloading door 21.

Thus, in one aspect of the present invention there is a rotating perforated cylindrical cage provided within a sealed container into which the suspect contaminated media is placed. The cylinder is rotated through a mechanical or other type of drive. The particulates are dislodged primarily through tumbling and secondarily through centrifugal force. Dislodged particles are entrained into an air stream and pass through a detector.

In another aspect of the present invention there is a shaker table driver, or similar physical vibration source, attached to a shallow box mounted on a slight angle,, which in a nonlimiting example may be approximately 20 degrees, within a container. The suspect contaminated media contained in a hopper above the shallow box with shaker driver, passes into the lower container only by sliding over the shallow fabricated box. The shaker table drivers vibrate the box and liberate the particulates. Air flow from within the vibrating box carries away the particulates to the detector.

In a further aspect of the present invention, which is a variation of that described in the preceding paragraph, uses a corrugated top surface for the vibrating box to aid in separation of the particulates from the suspect media moving over the box.

Previous attempts to handle articles having hazardous particulates therein or thereon integrated the liberation device with the detection device. The present invention separates the two processes and incorporates multiple liberation modules to produce a flow of "free from contaminant" mail available for sorting. This logistic method decreases cost of detection through multi-module application of the detection instrumentation and also allows technology refreshing of instrumentation while maintaining the liberation hardware. Implementing this disclosure eliminates decontamination of sorting machinery, equipment or process, in that, contaminated mail never reaches those devices.

Previously proposed systems modified mail sorting equipment to integrate detection at the sorter thereby slowing or stopping the sort process if a detection occurred. If detection occurred, the sorter had to be cleaned if detection was not a false positive.

By using the present invention, there is no interruption to the mail processing if detection occurs. No cleaning of the complex sorter is needed.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A system for detecting contaminants in or on objects, comprising:
   a. a movably mounted container for holding objects and having a plurality of perforations and an entrance opening through which objects may be placed into said container;
   b. a housing enclosing said container and forming a barrier to ambient air and having a sealable opening for inserting and removing objects from said container;
   c. means for moving said container within the housing to move objects therein for emitting particles which are in or on such object;
   d. means providing an air stream for moving air through said housing and container to entrain any emitted particles into the air stream; and
   e. a sensor for sensing contaminants in the air stream and providing a signal when a contaminant is sensed.

2. A system as defined in claim 1 wherein said container is a rotatable cage, or a vibrating box and said air stream providing means directs the air stream from the center of the container through the perforations in the container and into the housing.

3. A system as defined in claim 2 wherein the housing has an air inlet and an air outlet.

4. A system as defined in claim 3 wherein there are a plurality of containers and housings which are independently operable with respect to each other.

5. A system as defined in claim 4 wherein there are a plurality of sensors of different types forming a sensor suite.

6. A system as defined in claim 5 further comprising a discharge bin at the lower end of each housing and into which the objects therein are deposited when no contaminants are sensed.

7. A system as defined in claim 6 wherein the means for providing an air stream includes an air duct system which provides the air stream to the center of the container where it entrains emitted particles and directs the air stream past said sensor.

8. A system as defined in claim 6 wherein said container has a closable door for closing said entrance opening.

9. A system as defined in claim 8 wherein the means for providing an air stream includes an air inlet and an air outlet in said container.

10. A system as defined in claim 8 further comprising a neutralization assembly for injecting a contaminant neutralizer into the air stream when said sensor detects a contaminant.

11. A system as defined in claim 8 wherein said rotatable cage is six sided.

12. A system as defined in claim 11 wherein all six sides of said cage have perforations to permit air and particulates to pass therethrough.

13. A system as defined in claim 8 further comprising a controller for sequencing operations of said moving means, said air stream providing means, said sensor, and said discharge bin.

14. A system as defined in claim 13 further comprising:
   a neutralization assembly for injecting a contaminant neutralizer into the air stream when said sensor detects a contaminant, and said controller also controls the operation of said neutralization assembly.

15. A system as defined in claim 8 wherein said sensor suite comprises:
   at least one real-time sensor to sense said at least one contaminant, said contaminant being selected from the group of biological particles, chemical particles, and pathogens.

16. A system as defined in claim 8 further comprising an indicator subsystem which provides an indication when at least one contaminant is detected.

17. A method for detecting contaminants in and around objects, comprising the steps of:
   a. providing a chamber which may be sealed with respect to ambient air to create an enclosed atmosphere;
   b. loading a plurality of objects into or onto a perforated container disposed within the enclosed atmosphere;
   c. creating an air stream within the enclosed atmosphere;
   d. agitating the objects to cause the objects to emit particles therefrom into said air stream;
   e. testing the air stream to determine whether it contains any contaminants; and
   f. providing a signal when a contaminant is detected.

18. A method as defined in claim 17 wherein the agitation is provided by a rotating cage having openings in its sides.

19. A method as defined in claim 17 where the agitation is provided by a vibrating surface having openings therein.

20. A system as defined in claim 17, further comprising the step of discharging the objects from said chamber when no contaminants are detected.

* * * * *